(12) United States Patent
Doyle

(10) Patent No.: US 6,964,406 B2
(45) Date of Patent: Nov. 15, 2005

(54) VALVED MALE LUER

(75) Inventor: Mark C. Doyle, San Diego, CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 256 days.

(21) Appl. No.: 10/389,652

(22) Filed: Mar. 13, 2003

(65) Prior Publication Data

US 2003/0136932 A1 Jul. 24, 2003

Related U.S. Application Data

(63) Continuation-in-part of application No. 09/927,109, filed on Aug. 10, 2001, now Pat. No. 6,745,998.

(51) Int. Cl.[7] ........................ F16K 51/00; F16L 29/00; F16I 37/28
(52) U.S. Cl. ............................... 251/149.6; 251/149.4; 251/149.3; 604/241
(58) Field of Search ........................ 251/149.1, 149.3, 251/149.4, 149.6; 604/241

(56) References Cited

U.S. PATENT DOCUMENTS

| | | | |
|---|---|---|---|
| 2,931,668 A | 4/1960 | Baley | |
| 2,968,497 A | 1/1961 | Treleman | |
| 4,233,982 A | 11/1980 | Bauer et al. | |
| 4,245,635 A | 1/1981 | Kontos | |
| 4,379,458 A | 4/1983 | Bauer et al. | |
| 4,862,913 A | 9/1989 | Wildfang | |
| 5,065,783 A | 11/1991 | Ogle, II | |
| 5,098,385 A | 3/1992 | Walsh | |
| 5,203,775 A | 4/1993 | Frank et al. | |
| 5,211,634 A | 5/1993 | Vaillancourt | |
| 5,334,159 A | 8/1994 | Turkel | |
| 5,380,306 A | 1/1995 | Brinon | |
| 5,397,314 A | 3/1995 | Farley et al. | |
| 5,405,323 A | 4/1995 | Rogers et al. | |
| 5,405,333 A | 4/1995 | Richmond | |
| 5,492,147 A | 2/1996 | Challender et al. | |
| 5,514,117 A | 5/1996 | Lynn | |
| 5,520,665 A | 5/1996 | Fleetwood | |
| 5,540,661 A | 7/1996 | Tomisaka et al. | |
| 5,549,566 A | 8/1996 | Elias et al. | |
| 5,575,769 A | 11/1996 | Vaillancourt | |
| 5,578,059 A | 11/1996 | Patzer | |
| 5,584,819 A | 12/1996 | Kopfer | |
| 5,645,538 A | 7/1997 | Richmond | |
| 5,676,346 A | 10/1997 | Leinsing | |
| 5,738,144 A | 4/1998 | Rogers | |
| RE35,841 E | 7/1998 | Frank et al. | |
| 5,782,816 A | 7/1998 | Werschmidt et al. | |
| 5,806,831 A | 9/1998 | Paradis | |
| 5,839,715 A | 11/1998 | Leinsing | |
| 5,848,994 A | 12/1998 | Richmond | |
| 6,068,011 A | 5/2000 | Paradis | |
| 6,079,432 A | 6/2000 | Paradis | |
| 6,106,502 A | 8/2000 | Richmond | |
| 6,113,068 A | 9/2000 | Ryan | |
| 6,142,446 A | 11/2000 | Leinsing | |
| 6,206,860 B1 | 3/2001 | Richmond | |
| 6,299,132 B1 | 10/2001 | Weinheimer et al. | |
| 6,485,472 B1 | 11/2002 | Richmond | |
| 2003/0060779 A1 | 3/2003 | Richmond | |

FOREIGN PATENT DOCUMENTS

WO    WO 03/013646 A2    2/2003

Primary Examiner—F. Daniel Lopez
Assistant Examiner—John K. Fristoe, Jr.
(74) Attorney, Agent, or Firm—Fulwider, Patton, Lee & Utecht, LLP

(57) ABSTRACT

A male luer connector device that attaches to any standard female luer valve to open a flow channel between the two luers. The male luer is comprised of a tubular housing element, a resilient member contained within the housing and extending within an inner tubular portion defined in the housing, a resilient member that extends within the inner tubular portion of the housing, and a valve member attached to the resilient member that seals the tubular portion. When the male luer is engaged with any standard female luer, a female luer connector device drives the resilient member of the male luer into a compressed position to open the forward end of the male luer and permit liquid flow between the luers.

39 Claims, 10 Drawing Sheets

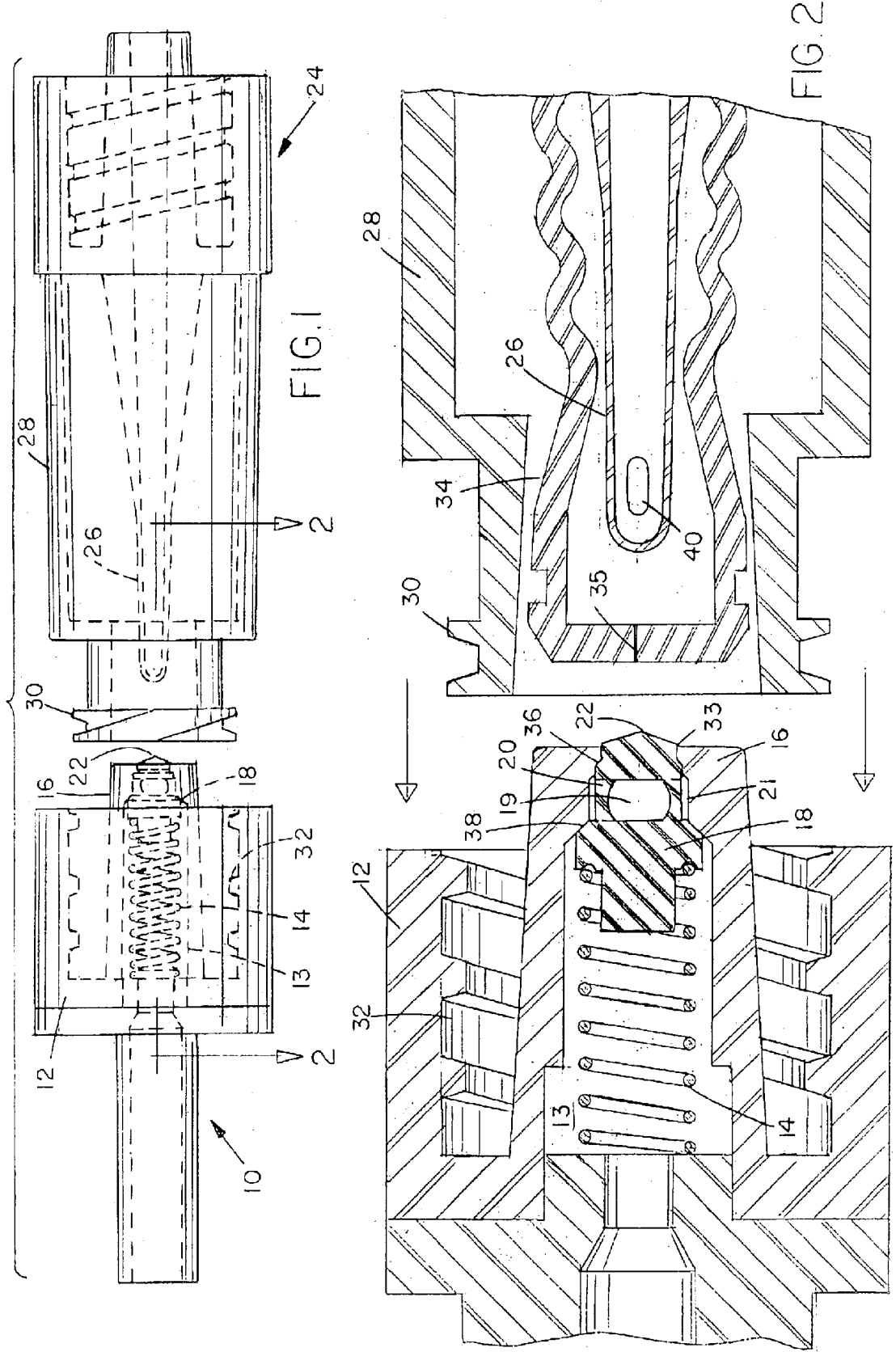

VALVED MALE LUER

CROSS-REFERENCE TO RELATED APPLICATION

This application is a continuation-in-part of application Ser. No. 09/927,109, filed on Aug. 10, 2001 now U.S. Pat. No. 6,745,998, of like title.

BACKGROUND OF THE INVENTION

This invention relates to an improved male luer connector device that attaches to a female luer valve to open a flow channel through the male luer. Once the engagement of the luers has been established, these valves are used to make connections in hospitals for intravenous (IV) devices in order to be used in medical liquid flow applications.

Luer devices are used in particular in a variety of medical applications where there is a desire to interconnect together male and female connector parts onto tubing material that is connected to an IV. The most common types of IV fluid exchanges use a syringe fitted with a nozzle that is designed to be received into a corresponding receiver attached to the IV device. The receiver often has a hollow tubular cannula or post that routes fluid into a line inserted into the IV extending into the patient's veins.

Typical luer connections utilize a male luer connector that is inserted into a female luer connector. The male luer connector is threaded onto corresponding threads of the female luer connector to engage the two so that fluid may be passed between them without escaping or leaking from the connection. Because these connections are subject to coming loose or disengaging, there is always a possibility that fluid being passed within these tubes can escape. When using hazardous drugs, such as those used for chemotherapy treatments, the possibility of escaping fluids can be a dangerous problem. Additionally, even if the fluid does not leak when the connectors are engaged, once they are disengaged, the residual amount of fluid remaining on the tip of the connectors can still be harmful. While this amount may be less than an amount escaping from the connectors, it can still be significant enough to cause harm to any person exposed.

Therefore, there is a need for a luer connection that securely contains the fluid materials included therein when luers are engaged to one another. There is also a need for a luer connection that seals off the male luer connector in a male-female connection so that users of the connector are protected from hazardous drugs that remain on the luer tip surface when disengaged.

SUMMARY OF THE INVENTION

It is an object of the present invention to provide a new and improved male luer connector device for engagement with a female luer valve for connection to an IV or other fluid-type connections.

According to one aspect of the present invention, a male luer connector device is provided for establishing a connection with a corresponding female luer valve, which may or may not have a central post, which is exemplified by a core rod or cannula. The male luer connector device comprises a housing, an inner chamber, a resilient member, and a valve member. The housing has an outer tubular portion and an inner tubular portion and first and second necked areas and the valve member has a tip that seals the forward end of the inner tubular portion. The resilient member can be elastically displaced and extends within the inner tubular portion of the housing.

The male luer is inserted into a corresponding female luer and the two are engaged. When the female luer engages with the male luer, a contact member, which may be a core rod or cannula within the female luer or an end face of a portion of the female luer structure, of the female luer pushes first against the tip of the male luer. The tip then moves and collapses the valve member at the first necked area. Further engagement continues to move the valve member and then collapses the resilient member at the second necked area. Once the luers are entirely in the engaged position, fluid may flow between the luers and enter or exit the female luer via an inlet port. If it is desired, the male luer valve does not have to be contained within a housing element. Instead, it may be self contained or additionally, those skilled in the art will recognize that the male luer valve can be contained within other enclosures.

According to another aspect of the present invention, a male luer connector device is provided that comprises a resilient member, a inner chamber, and a valve member. This embodiment functions identically to the prior embodiment with the exception that the valve member is either integrally formed with the resilient member or can be abutting the resilient member. The resilient member can be formed of an elastomeric material or can be a spring formed of many different materials. The inner chamber is then sealed off by the integrally formed member. When an appropriate female luer valve is engaged with the male luer, the integrally formed member collapses in order to permit liquid flow between the two luers. If desired, this embodiment may alternatively contain a housing.

Where the female luer contains an internal core rod or cannula, that serves as the contact member to force back the resilient member in the male luer and open the valve portion of the male luer to permit fluid flow between and through the joined luers. In a different embodiment, a male luer is described that can work with a female luer that does not contain a cannula or core rod. This luer comprises a housing, a first tubular member, a resilient member, a valve member, and optionally a slidable sleeve member. The housing has an outer tubular wall and a first tubular member which extends co-axially within the housing. The first tubular member has at least one axially extending slot and a forward end having a valve seat. The valve member is located at the end of the resilient member for sealing engagement of the valve seat. The resilient member has at least one guide portion that extends radially outwardly through the axial slot. If there is a sleeve member it is slidably mounted over the first tubular member and the outer tubular wall so that the sleeve traps the guide portion. In other embodiments the resilient member is self-guiding along the male luer structure or may be guided by the axially extending slot. When the female luer is engaged to the male luer, the housing of the female luer engages the sleeve and slides it rearwardly into the male luer housing. This pushes the resilient member and the valve member rearwardly into a retracted position to allow liquid flow between the two luers. Once again in this embodiment, the housing element does not have to be present. Instead, the male luer valve may be self contained or contained within other types of enclosures.

The configurations of the present invention described herein are advantageous for many reasons. When the male luer is mated or disengaged with an appropriate female luer valve, the male connector seals off to protect any user from exposure to potentially hazardous fluids. The valve contained on the end of the male luer is self-closing so that it ensures that minimal amounts of fluid remain on any exposed surface of the luer. This advantage helps ensure hazardous drugs, such as those used in chemotherapy treatments, do not remain on the luer. Also, bodily fluids, such as blood, do not remain on the luer in order to minimize exposure to potentially diseased blood. The valve design allows either mutual swabbing or one-sided swabbing because there are minimal crevices on the luer and the tip member is substantially flush. Additionally, in one embodiment, the configuration of the male luer provides another advantage in that it creates a vacuum effect on the tip of the luer when the male and female luer are disengaged. This vacuum tip feature acts to minimize residual fluid on any surface and therefore minimizes all types of exposure.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 is a side view of the two components of the male to female luer connection of the luer fitting;

FIG. 2 is an enlarged sectional view taken on line 2—2 of FIG. 1;

DETAILED DESCRIPTION OF THE DRAWINGS

Figure 3:
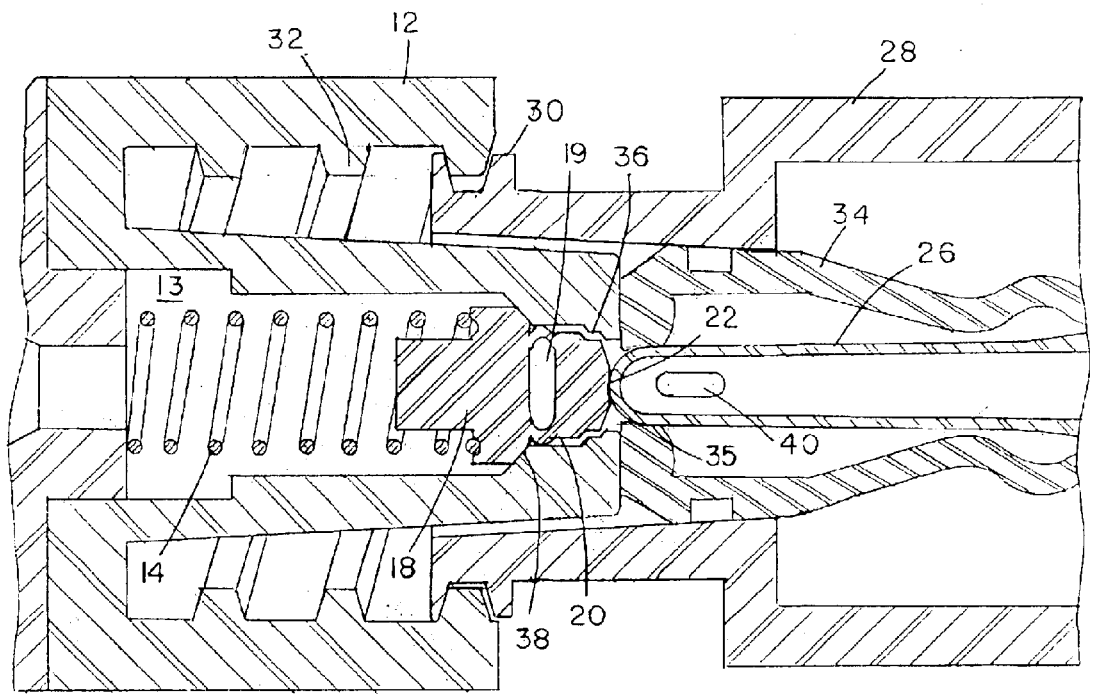
FIG. 3 is a view similar to FIG. 2, with the components partially engaged.

FIG. 1 is a side view of the two components of the male to female luer connection of the luer fitting. The fitting is comprised of a male luer 10 that is intended to engage with a female luer that has an existing flush top female luer valve. The female luer 24 is not limited to a particular type but an exemplar luer is illustrated here. The female luer illustrated here is one where the valve shuts off. This female luer 24 contains a housing element 28 with a cannula or post 26. On the outer surface of the forward end of the housing 28 there are threads 30 that permit engagement of the female luer 24 with the male luer 10. In this embodiment the male luer 10 is comprised of a housing element 12. The inner wall of the housing 12 contains threads 32 that engage the complimentary threads 30 of the female luer connector. Housing 12 has an inner tubular portion 16 of reduced diameter that projects forwardly that has a first necked area 36 and a second necked area 38 (See FIG. 2). The inner tubular portion defines an internal chamber 13 with a forward opening 33 (See FIG. 2). A valve member 18 is biased into an extended position sealing opening 33 by resilient member or spring 14. Spring 14 acts between distal end of chamber 13 and valve member 18. (As used herein, "distal" is the rearward end of the male luer and "proximal" is the forward end, i.e., the left and right ends in the views as illustrated in FIGS. 1 and 2.) Valve member 18 includes a resilient portion 20 and a forward tip member 22. FIG. 1 illustrates the two luers 10, 24 in the unengaged position. Other types of female luer valves that do not contain a cannula or post. By way of example, U.S. Pat. No. 5,676,346 by Leinsing and U.S. Pat. No. 5,782,816 by Werschmidt illustrate these types of luer valves.

FIGS. 2 to 5 illustrate the male luer 10 and the female luer 24 as they become engaged with one another. FIG. 2 illustrates the two luers 10, 24 when they are completely unengaged. The cannula or post 26 may have an opening 40 for entrance and exit of fluid between the two luers. Other duct systems (not shown) are possible and may be used. The cannula or post 26 is mounted in a chamber within a sleeve 34. This sleeve 34 can be made of rubber or any other suitable resilient material and serves as a valve member stopper. Sleeve 34 has a forward end opening 35 which is sealed shut in the unengaged position of FIG. 2. The male luer has a forward end that has a first necked area 36 and a second necked area 38 spaced rearwardly from the first necked area 36. FIG. 3 illustrates the male luer 10 beginning to be inserted into the female luer 24. Once the threads 30, 32 begin to engage, the forward end 33 of housing 12 pushes the sleeve 34 back until the opening 35 is forced to open over the end of the cannula 26. The cannula or post 26 then comes into contact with the tip of valve member 18 and begins to push it rearwardly so that the cannula or post 26 displaces the valve element front section 22. This movement begins to separate the seal surface of the first necked area 36 from its seat. As the tip member 22 begins to be pushed back, the second resilient portion 20 is collapsed, compressing the valve element cavity 19. This unseals the first necked area 36 and displaces the liquid contained within the cavity 19. This displaced liquid flows temporarily into the female luer valve 24. As this pressure is applied, the valve member is compressed and pushed further inwardly into chamber 13.

Figure 4:
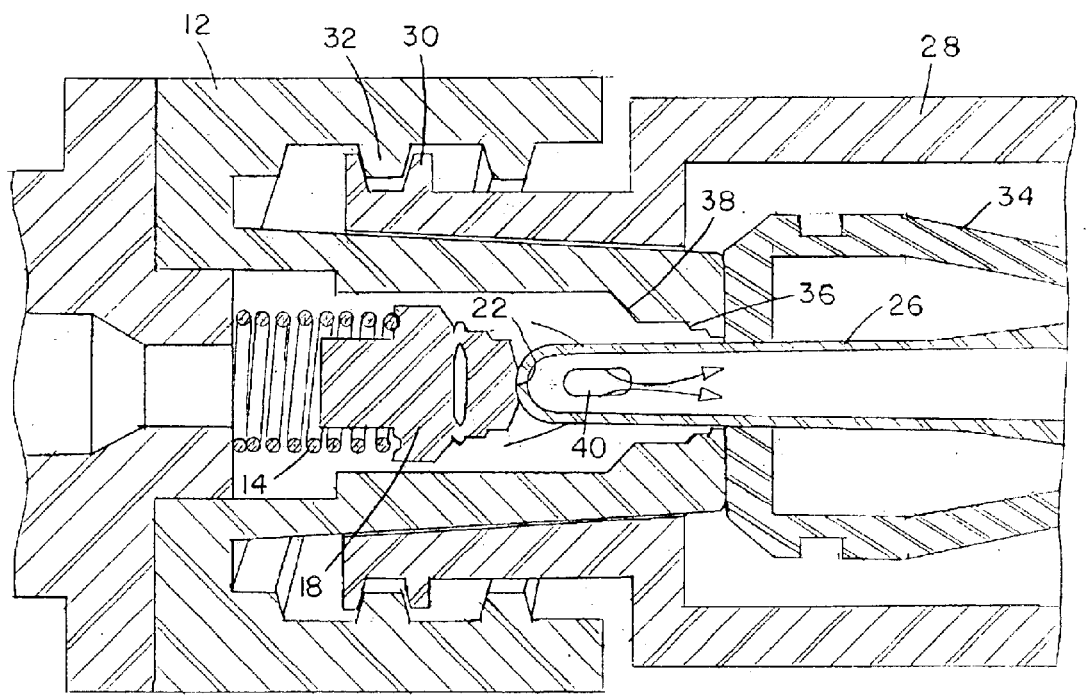
FIG. 4 is a view similar to FIG. 3, with the components fully engaged.

FIG. 4 illustrates the positioning of the luer members when the female 24 and male 10 luers have been even further engaged. The cannula or post 26 begins to push even more onto the tip member 22 and collapse the first resilient member 14 so that the second necked area 38 is unsealed. At this point, more liquid is displaced by the further insertion of the cannula or post into the vacuum section 21 of the male luer as indicated by the arrows in FIG. 4. The opening 40 on the cannula or post 26 permits fluid to pass into and out of the female luer 24. This displaced liquid creates the volume which will be refilled when the action is reversed.

Upon disconnection of the male luer 10 valve from the female luer valve 24, the volume of liquid that was displaced during the connection of the two valves is restored to the original positions, thus creating a relative vacuum. When the female luer 24 is removed from the male luer 10, the main seal created by the second necked area 38 makes contact with its seat. This isolates the vacuum section 21 from the upstream liquid. As the cannula or post 26 is withdrawn, cavity 19 is restored as resilient portion 20 resiles to its uncollapsed natural shape. As this restoration occurs, liquid is drawn into cavity 19. Because the second necked area 38 is closed, this liquid will be drawn from the interface between the male luer 10 and the female luer 24. This effect is enhanced by the volume represented by the cannula or post 26, which must be replaced as the cannula or post 26 is withdrawn. The relative vacuum created will attempt to draw liquid into the vacuum section until the seal surface of the first necked area 36 again contacts its seat.

Figure 5:
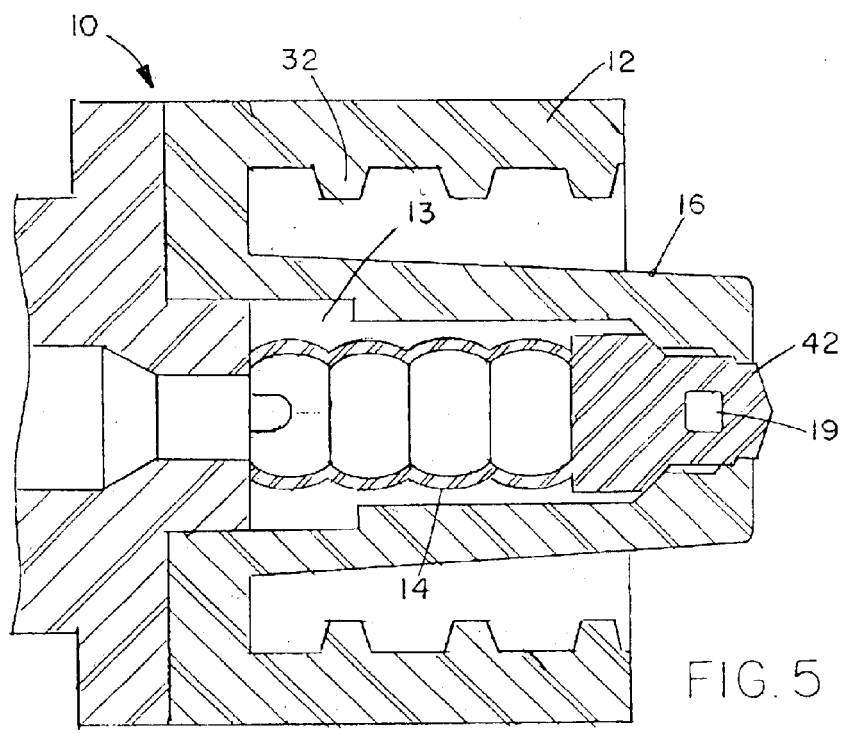
FIG. 5 is a view similar to a portion of FIG. 2, showing an alternative integrated spring member.

FIG. 5 illustrates the same type of dual stage valve as above only that it is formed with the spring 14 integrally connected to the valve member 42. The housing 12 contains the inner sleeve 16 and positioned inside of the inner sleeve 16 is an inner chamber 13. The function of this embodiment is the same as the previously described embodiments with the exception that the spring 14 can be comprised of elastomeric or other types of material that are integrally connected with the valve member 42.

Figure 6:
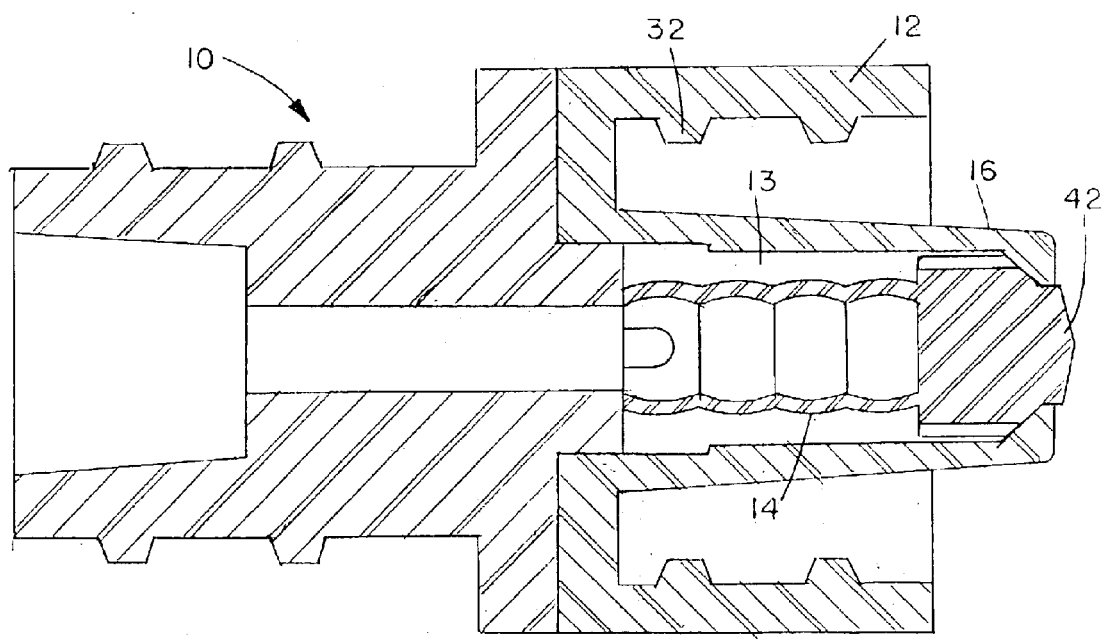
FIG. 6 is a view similar to FIG. 5, showing an alternative single stage valve.
Figure 7:
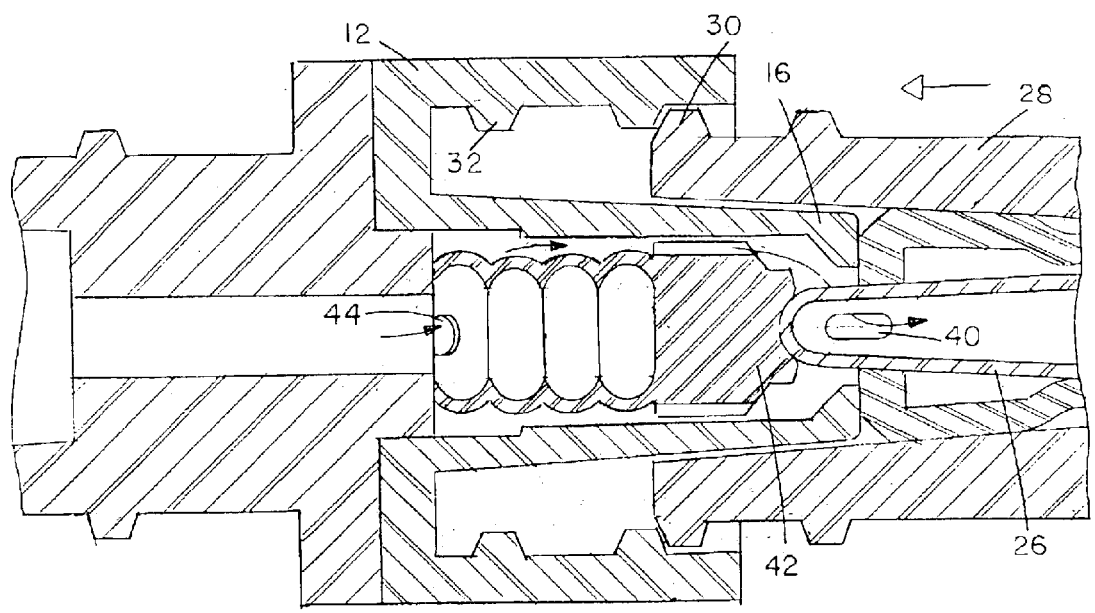
FIG. 7 is a view similar to FIG. 6, showing the valve opened.

FIGS. 6 and 7 illustrate a male luer according to another embodiment of the present invention. This apparatus is a single stage luer valve with an integral resilient member. In this embodiment, the male luer has a housing 12 with threads 32 on the inner wall of the housing for engagement to the complimentary threads on the female luer 30. The inner chamber 13 is sealed by a valve member 42 that is integrally formed with the resilient member and the tip. This new valve member 42 therefore functions as in the previous embodiment except that all members are formed in one piece, rather than including a separate resilient member. This embodiment demonstrates a single stage luer valve in that once the female luer engages with the valve member 42, the member 42 moves as a single piece rather than as several different pieces as described above. FIG. 7 illustrates the luer of FIG. 6 engaged with a female luer 24 and permitting fluid flow. Once the two luers 10, 24 are engaged, the cannula or post 26 of the female luer 24 collapses the valve member 42 and permits fluid flow via the opening 40 in the cannula or post 26 and also via an opening 44 in the rear end of the valve member 42.

Figure 8:
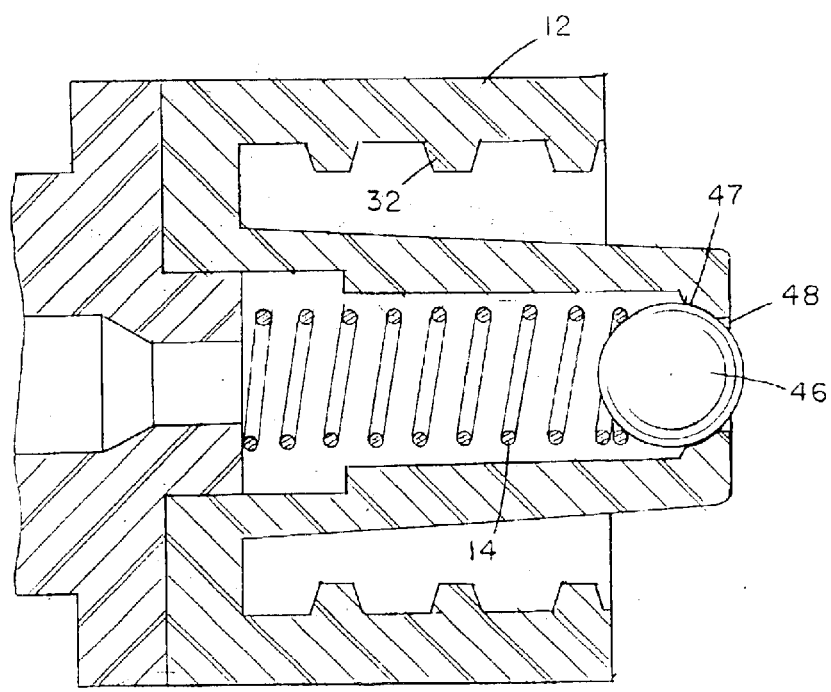
FIG. 8 is a view similar to FIG. 5, showing a ball type valve.

FIG. 8 illustrates another embodiment of the present invention. In this embodiment, the housing 12 of the male luer is similar to the previous embodiments. Additionally, contained within the inner sleeve 16 is a resilient member or spring 14. However, in this embodiment, the valve contained on the end of the resilient member is shown as a ball 46. This ball may be made of various types of materials as for example, elastomeric material. Additionally, the forward end opening of chamber 13 is exemplified as a part-spherical seat 47 to accommodate for ball valve 46. Those skilled in the art will recognize that the valve contained on the end of the resilient member or spring 14 can be of a variety of shapes. However, the shape of the tip of the male luer 10 needs to be one that corresponds to the shape of the tip of the female luer 24.

Figure 9:
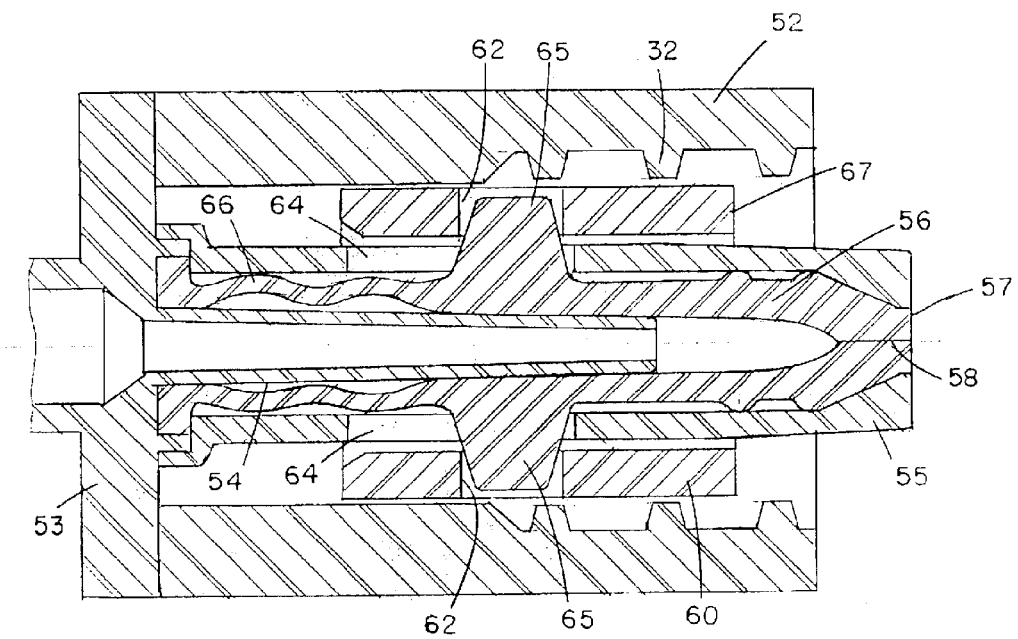
FIG. 9 is a sectional view showing an alternative slide actuated valve.
Figure 10:
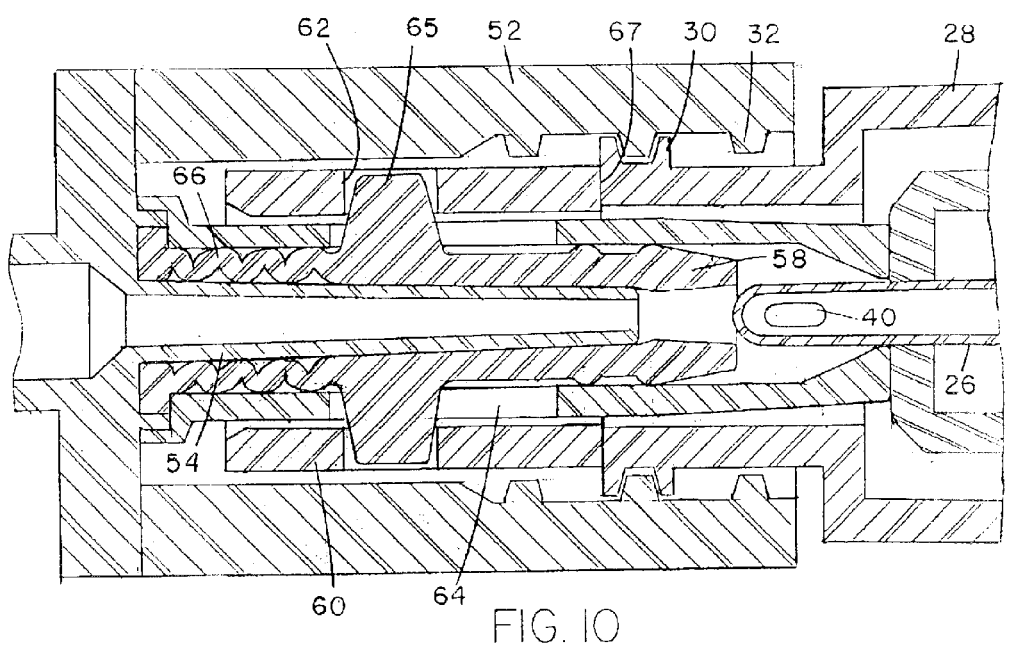
FIG. 10 is a view similar to FIG. 9, showing the valve opened.

FIGS. 9 and 10 illustrate a modified connector according to yet another embodiment of the present invention, in which a modified male luer is releaseably securable to the female luer 24 of the previous embodiments. The modified male luer comprises a housing with a cylindrical outer wall 52 and an inner tubular support 54 which projects into the cylindrical housing from rear end 53 and extends along part of the length of the housing. Outer wall 52 has internal threads 32 for engaging the female luer threads 30 and a larger diameter than the inner support 54 which extends from the rear end 53 of the housing and projects out of the forward end of the housing. A resilient sleeve or bladder member 56 is secured between the tubular member 55 and support 54 at its rear end, and projects forwardly within tubular member 55 to its forward end opening 57. Bladder member 56 has a forward end opening 58 which is sealed shut by the inwardly tapered end portion of the tubular member 55 when in the extended, unconnected position of FIG. 9. The forward end portion 58 of bladder member 56 acts as a valve to seal the end opening 57 of the male luer in the position illustrated in FIG. 9.

Tubular member 55 of the male luer is of smaller diameter than the inner cylindrical wall 52 of the housing, to leave an annular gap between the member 55 and inner wall 52. A sliding sleeve 60 is slidably mounted over the tubular member 55 in this annular gap. Sleeve 60 has diametrically opposed openings 62, and the tubular member 55 has opposing elongate, axially extending slots 64. Oppositely directed guided portions 65 (e.g., tabs, wings or fins) on the inner bladder or sleeve member 56 project radially outwardly through the slots 64 and into the openings 62. Thus, when the sleeve is in the fully extended position of FIG. 9, it will pull the sliding sleeve forwardly into the illustrated position. The corrugated portion 66 of bladder member 56 acts as a spring to bias the forward end of the bladder member 56 and the sliding sleeve 60 into the extended position.

FIG. 10 illustrates a female luer 24 connected to male luer 50. As the forward end of the female luer housing is threaded into the cylindrical wall of the male housing, it will engage the forward end 67 of the sliding sleeve 60, urging the sleeve, and thus the bladder member 56, rearwardly and moving the forward end portion of the bladder member out of sealing engagement with the forward end opening of tubular member 55. This permits the forward end opening 58 to spring open, as indicated. At the same time, the forward end of tubular member 55 will force the sleeve 34 in the female luer rearwardly so that it passes over the end of cannula 26, which then extends into the open forward end of the tubular member. This allows fluid flow through the two luers, via the inner tubular support, open end 58 of the bladder member 56, and the openings 40 in the cannula 26. When the luers are disconnected, the compressed corrugated portion 66 of the bladder member 56 urges the forward end portion to move back into sealing engagement with the forward end of the tubular member 55, preventing any fluid leakage.

Figure 11:
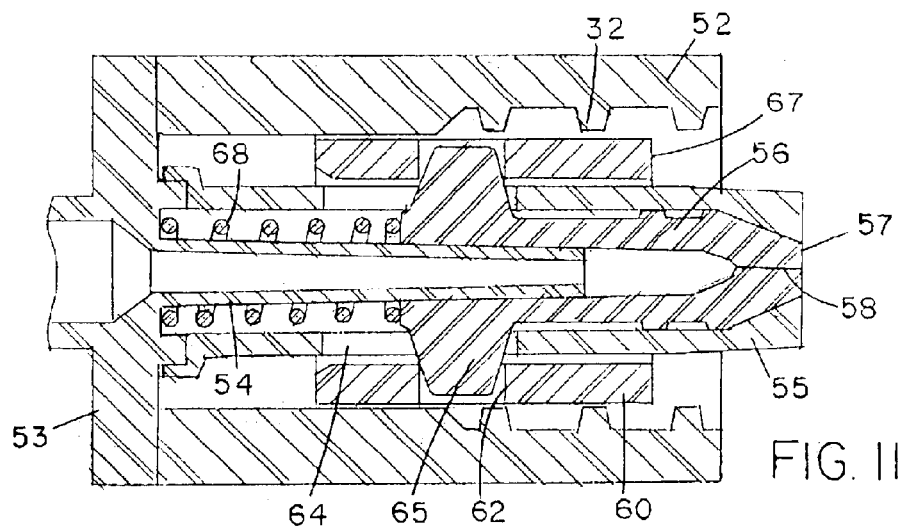
FIG. 11 is a view similar to FIG. 9, showing an alternative slide actuated valve.

FIG. 11 is a view similar to FIG. 9, showing an alternative slide actuated valve except that the resilient sleeve or bladder member 56 does not have a corrugated portion and instead has a separate spring member 68. The spring member 68 can any type as for example, those made of metal or elastomeric material. The function of the male luer valve is the same, it is merely the spring member 68 that replaces the previous corrugated member.

Figure 12:
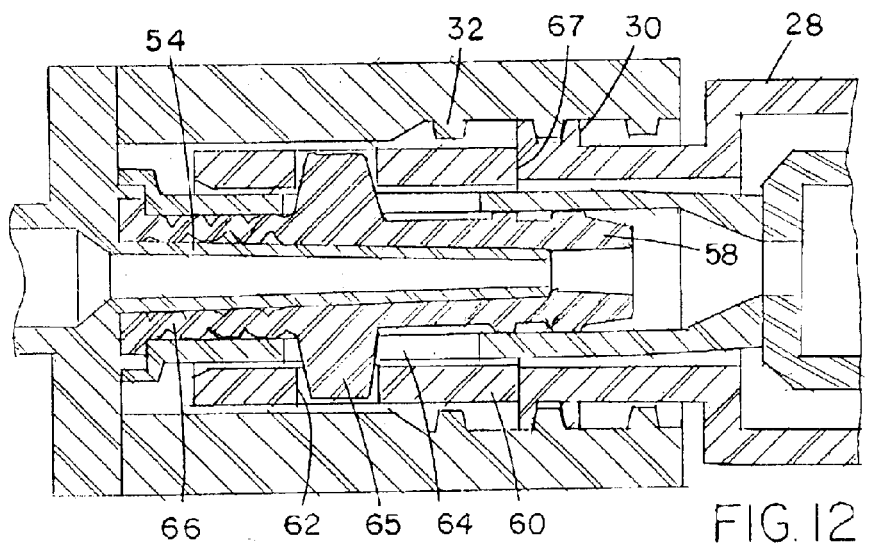
FIG. 12 is a view similar to FIG. 10, showing an alternative valve for use with a female luer valve that does not have a cannula or post.

FIG. 12 is a view similar to FIG. 10, showing an alternative valve for use with a female luer valve that does not have a cannula or post. The outer surface of the forward end of the housing 28 engages and compresses the forward end 67 of the sliding sleeve 60 of the male luer valve. As the forward end of the female luer valve housing 28 continues to further displace the sliding sleeve 60, the bladder member 56, continues to move rearwardly and moves the forward end portion of the bladder member out of sealing engagement with the forward end opening of the tubular member 55. This permits the forward end opening 58 to spring open. This allows fluid flow through the two luers, via the inner tubular support, open end 58 of the bladder member 56. Once the luers are disconnected, the sealing engagement as previously described once again occurs.

Figure 13:
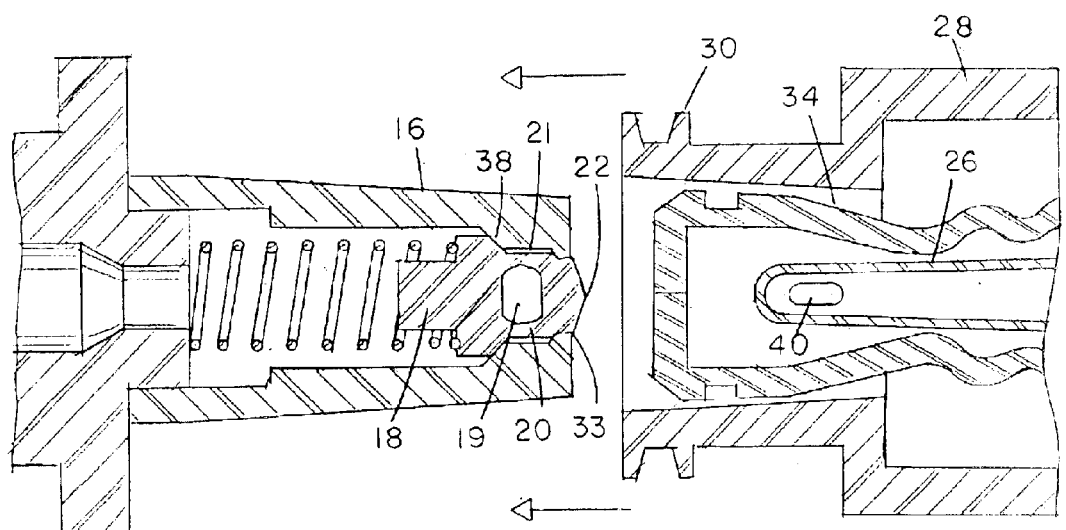
FIG. 13 is an illustration of a male luer valve that does not contain a housing element.

FIG. 13 is an illustration of a male luer valve that does not contain a housing element. This view is similar to FIG. 2 except that the male luer valve is not contained within a housing element and instead can be self-sustained. However, the function of the male luer valve is the same as that explained for FIG. 2 only that the engagement with the female luer housing does not occur with the male luer housing.

Figure 14:
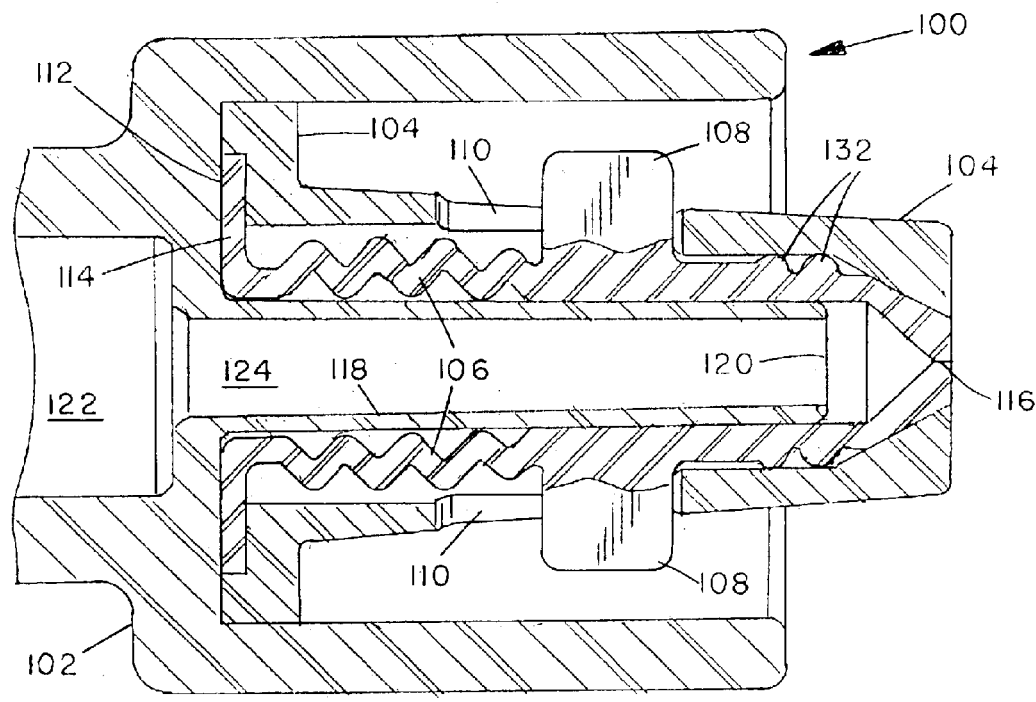
FIGS. 14 and 15 are views similar to FIG. 11 illustrating a male luer which does not contain a sleeve and showing the movement from a closed position (FIG. 14) to an open position (FIG. 15) for the male luer during contact with a female luer having no core rod or cannula.
Figure 15:
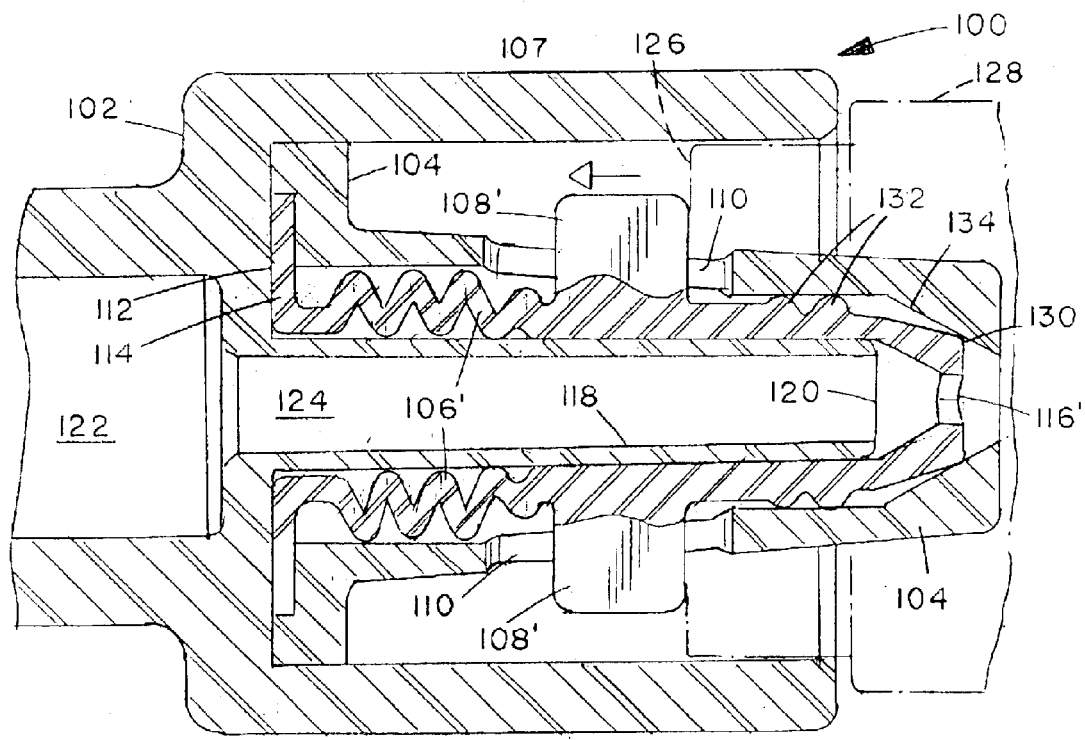

FIGS. 14 and 15 illustrate an embodiment of a male luer 100 which does not contain a sliding sleeve 60. The luer housing 102 has a tubular projecting conduit 118 over which is positioned resilient sleeve or member 106. The base 114 of resilient member 106 is butted against the interior end wall 112 of housing 102 and secured in place by the inner end of tubular projecting member 104. The resilient member 106 has one or more laterally projecting fins 108 which are disposed respectively in slots 110 in the tubular portion of member 104. When the male luer is closed (FIG. 14) the opening at the tip 116 of resilient member 106 is closed, sealing off the open end 120 of the male luer 100. When the male luer is engaged by a female luer 128 which has a contact surface 126 but no central core rod or cannula (FIG. 15) the surface 126 engages the fins 128 and movement of the male luer into the female luer causes the fins to move backward into housing 102 as indicated by arrow 107 with the fins 108 guided within the slots 110 as shown at 108' to compress the bellows portion of the resilient member as shown at 106'. This opens the tip as shown at 116' to allow fluid flow through opening 120 into the flow channels 124 and 122 of conduit 118 and housing 102 respectively. The peripheral projections 132 function as O-ring seals and when the luers are engaged the projecting front edge 130 of the resilient member 106 engages the inner sloped surface 134 of member 104 to provide a sealing or "stopper" effect and keep the O-ring seal area free of the fluid flow and dry.

For simplicity in a number of the Figures the female luer 128 is not itself shown and only the movement of elements of the male luer 100 are illustrated. It will be understood that such movement is the result of the male/female luer engagement in the manner illustrated in other Figures such as (but not limited to) FIGS. 2, 3, 12 and 15. Similarly, threads or other securing devices to retain the male and female luers in their engaged positions during flow of fluid through them are also for simplicity not shown in all Figures, but it will understood that such are present as illustrated in (but not limited to) FIGS. 2, 3, 4, 10 and 12.

Figure 16:
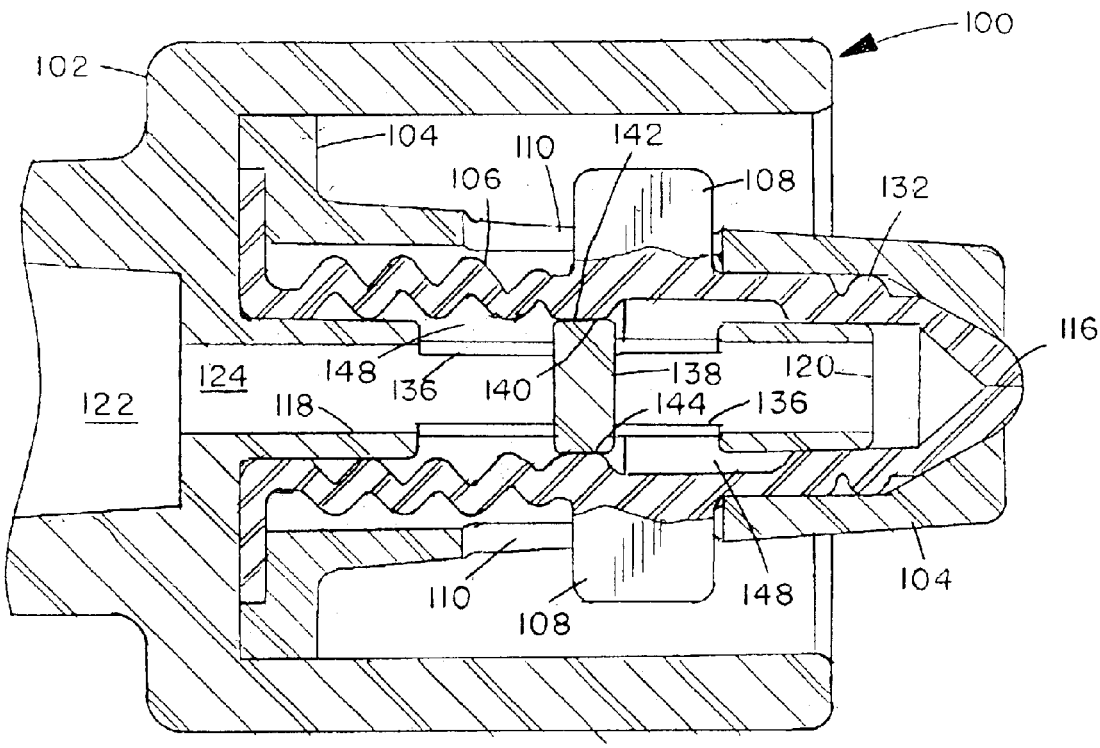
FIGS. 16 and 17 are views similar to FIGS. 14 and 15 illustrating a male luer having a central sealing member internally of the resilient member and showing the movement from a closed position (FIG. 16) to an open position (FIG. 17) for the male luer during contact with a female luer having no core rod or cannula.
Figure 17:
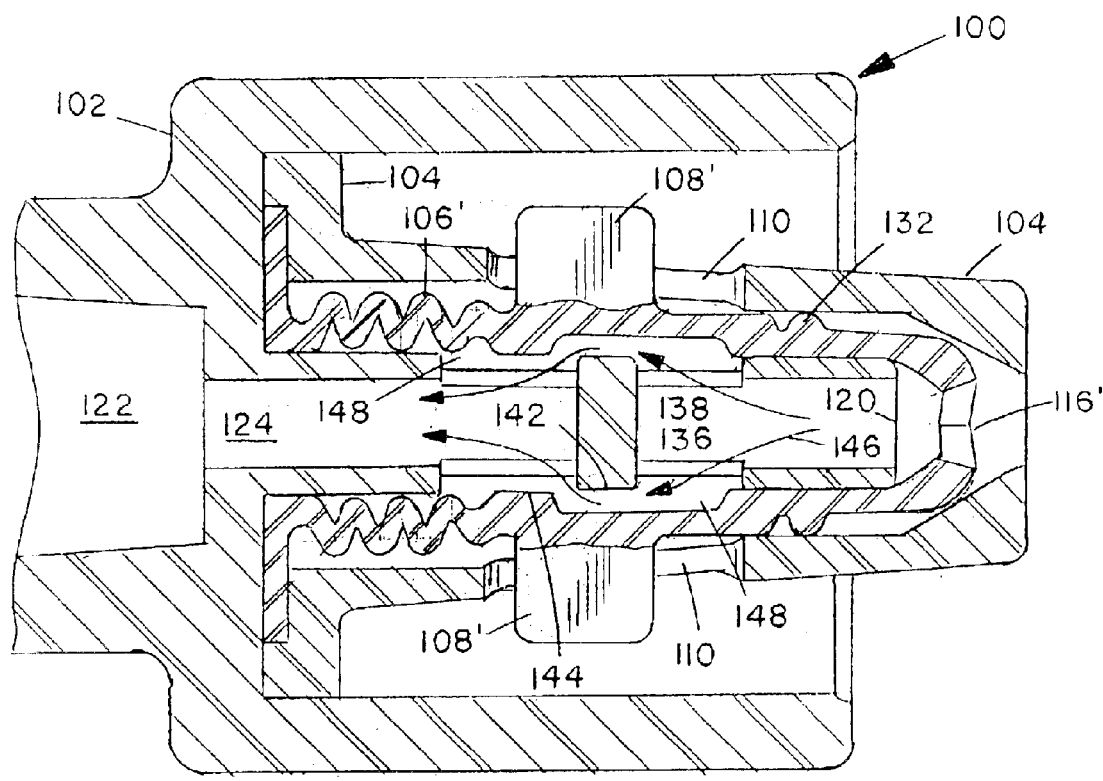

FIGS. 16 and 17 illustrate an embodiment similar to that of FIGS. 14 and 15, but in which there is an internal plug 138 within the conduit 118 with channels 148 past the plug 138. These channels can be formed in the wall of conduit 118 or can be formed by having plug 138 mounted on spaced apart supports (not shown) connected to conduit 118, or in any other convenient manner. The peripheral surface 142 of plug 138 contacts radial land 144 on the inner surface of resilient member 106 as shown at 140 when the male luer is closed (FIG. 16). When the male luer enters the female luer the contact surface 126 contacts the fins 108 and pushes them backward as shown at 108' in FIG. 17, thus compressing the resilient member as shown at 106' and displacing the land 144 from contact with the surface 142 of the fixed plug 138. Compression of the resilient member also opens tip 116 of the resilient member as shown at 116'. Fluid flow through opening 120 into conduit 124 and around plug 138 through channels 148 as shown by arrows 146 is also effected. The axial position and width of land 114 can be varied to determine when contact with the plug edge 142 is made or lost, thus determining when the luer opens or closes, and also to provide a vacuum effect to prevent or minimize backflow of fluid.

Figure 18:
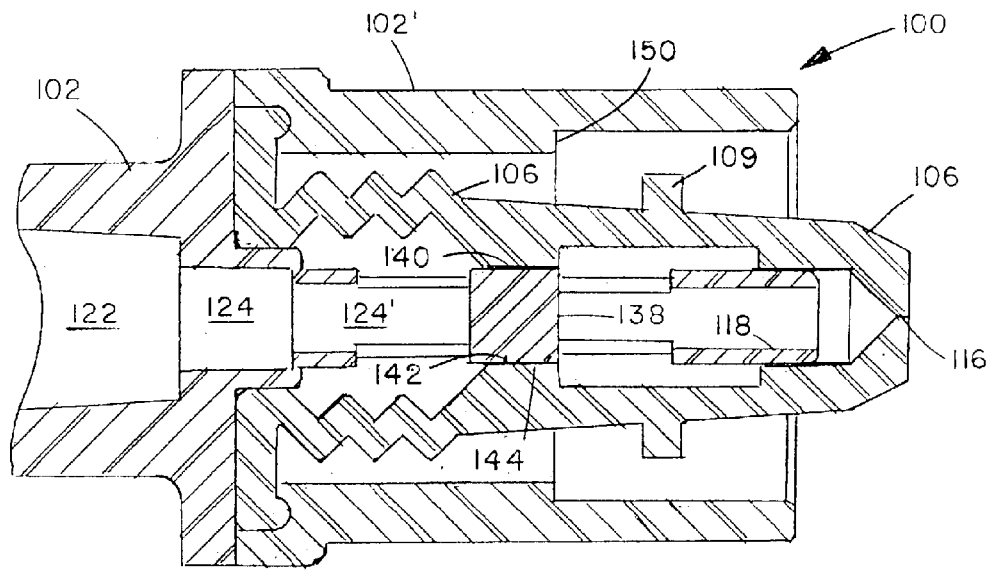
FIG. 18 is a view similar to FIG. 11 illustrating a male luer which has a peripheral flange incorporated into the resilient member which upon contact with the contract surface of a female luer (which has no core rod or cannula) is urged backwards causing the resilient member to retract and open.
Figure 19:
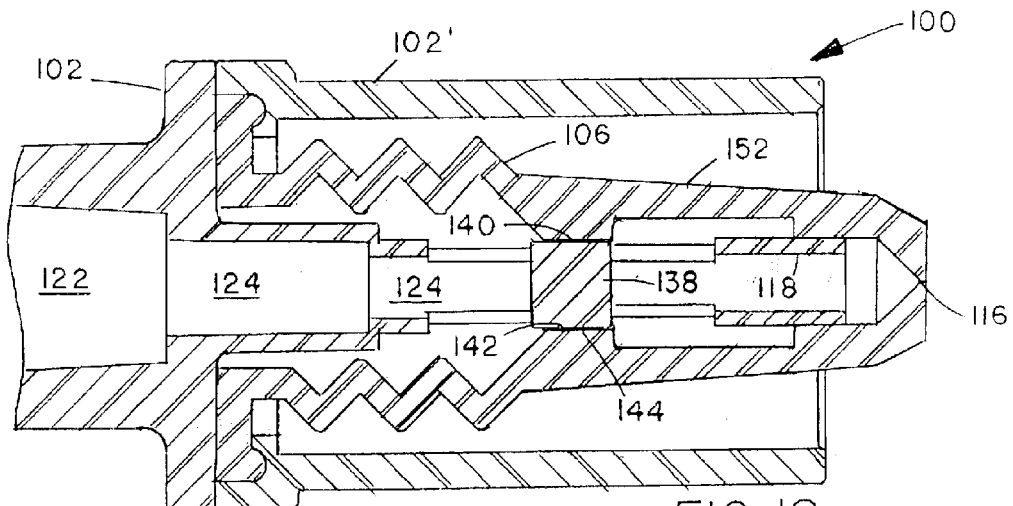
FIGS. 19, 20 and 21 illustrate appearance and operation of male luers which have resilient members with smooth outer contact surfaces which upon contact with the contract surface of a female luer (which has no core rod or cannula) provide a sufficiently frictional connection such that the resilient member is urged backwards causing it to retract and open.
Figure 20:
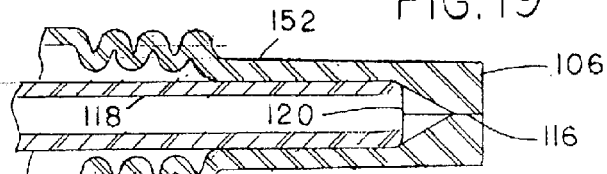
Figure 21:
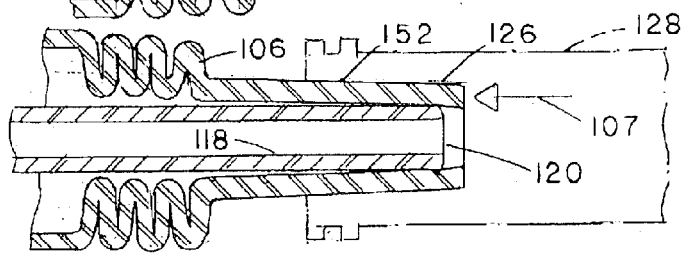

FIGS. 18–21 illustrate embodiments of a "soft" male luer 100 in which the engagement with the female luer 128 results in the contact area 126 of the female luer being the interior surface of the luer which is in contact directly with the exterior surface 152 of the resilient member 106, as illustrated in FIG. 21. In FIG. 18 two optional elements are shown: shoulder 150 and projections 109 which can be fins such as 108, a peripheral flange, protruding structure which can engage the contact surface of the female luer. The shoulder 150 can be a continuous radial shoulder within the portion 102' of the housing 102 or it can consist of spaced-apart projections aligned radially within portion 102'. (Portion 102' is shown in FIGS. 18 and 19 as a member separate but attached to the rest of housing 102, but it can also be integral with the rest of housing 102.) Shoulder 150 serves as a limiting device to engage contact surface 126 of the female luer 128 and stop the relative movement of the two luers, thus limiting the depth to which the male and female luers can be engaged. Projections 109 can assist the compressions of the resilient member 106 by sharing engagement with the contact surface 126 with the surface 152 of the member 106. The tip area 116 of the member 106 can be thickened as shown in FIGS. 18 and 19 to provide some expansion into the engaging neck of the female luer and thus create an additional sealing effect.

In FIGS. 20 and 21 the soft male luer 100 is illustrated as having an optional extended housing 102, such that engagement of the surface 152 of member 106 in contact with surface 126 provides the entire engagement of the male and female luers. That engagement and the compression of member 106 over the rigid conduit 118 allows opening of tip 116 and flow through end 120.

Figure 22:
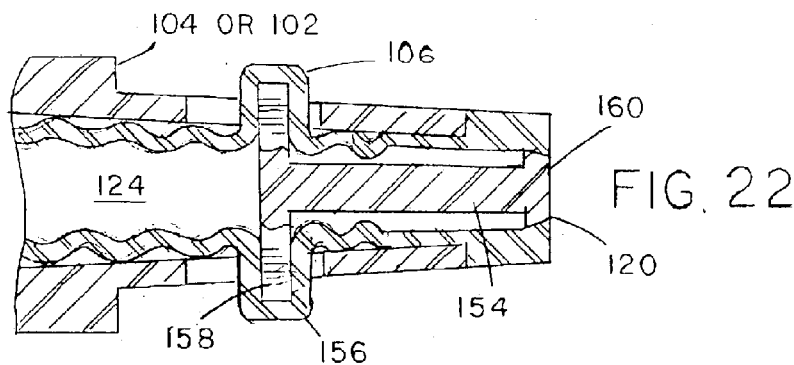
FIGS. 22 and 23 are views similar to FIGS. 16 and 17 illustrating a male luer having a central sealing member internally of the resilient member which has a radially extending portion which protrudes into the wall of the resilient member and extends it outward, allowing it to extend into or through a guide in the housing of the male luer, which guide is engaged by a contact surface of a female luer having no core rod or cannula, such engagement causing the resilient member to retract and open to permit fluid flow between and through the luers.
Figure 23:
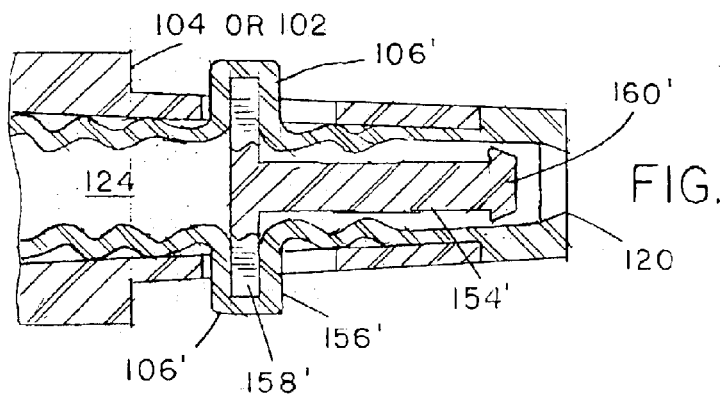
Figure 24:
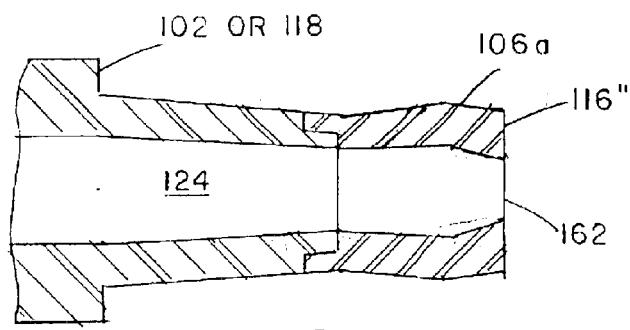
FIGS. 24, 25, 26 and 27 are side elevation views (FIGS. 24 and 26) and end elevation view (FIGS. 25 and 27) of another embodiment of a resilient member of a male luer which has a slightly bulbous tip with a slit opening, which slit is compressed and opened during contact with the interior surface of a female luer with a generally conical contact recess.
Figure 25:
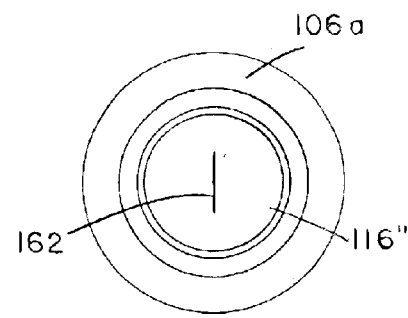
Figure 26:
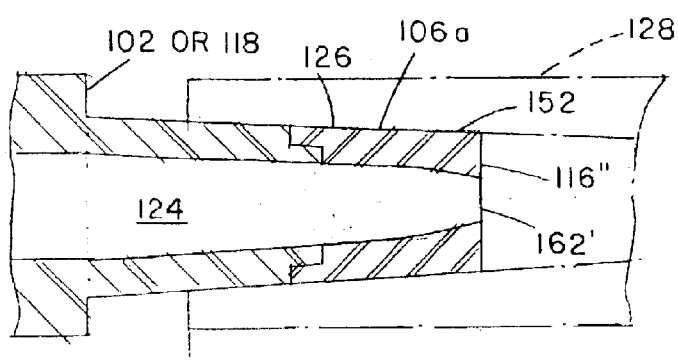
Figure 27:
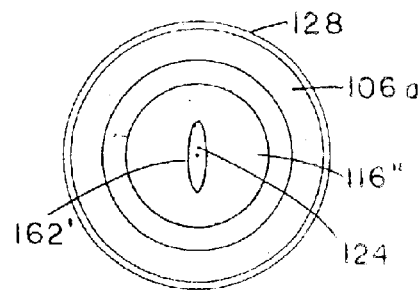

Additional embodiments are shown in FIGS. 22–27. In the embodiment of FIGS. 22 and 23, an internal plug 154 similar in function to that of valve member 42 is shown. The plug 154 has a integral fins or radial flange 158 which is inserted into a radial pocket 156 in resilient member 106. Engagement with the female luer causes the female luer's contact surface to push the resilient member 106, its pocket 156 and fins or flange 158 backward as shown as 106', 156' and 158' respectively, thus withdrawing plug head 160 of plug 154 to the position shown at 160' thus opening end 120 for flow into conduit 124.

FIGS. 24–27 shown a shaped resilient member 106a which has a slit 162 in its tip 116". When contacted by the female luer 128, frictional engagement of the outer surface 152 of the resilient member 106a with the contact surface 126 of the female luer causes the resilient member 106a to deform as shown in the Figures, thus opening slit 162 as shown at 162' to allow fluid flow into conduit 124.

The various embodiments of the male luer described above provide for automatic sealing of the end opening in the male luer as the male and female luers are disconnected, reducing the risk of an operator coming into contact with the potentially hazardous fluid flowing through the connector.

Although some exemplary embodiments of the invention have been described above by way of example only, it will be understood by those skilled in the field that modifications may be made to the disclosed embodiments without departing from the scope of the invention, which is defined by the appended claims.

I claim:

1. A male luer comprising:
    a tubular conduit having a forward end;
    a resilient member extending coaxially with the tubular conduit opposite rearward and forward ends; and
    a valve member at the forward end of the resilient member, the valve member openably sealing the forward end of the tubular conduit;
    such that when the male luer is inserted into a female luer, contact with the female luer drives the resilient member into a compressed position to open the valve member of the male luer and permit flow from one luer to another, with the liquid transiting the male luer traveling in a generally axial path through the tubular conduit of the male luer to or from the female luer.

2. The male luer as claimed in claim 1, further including the tubular conduit having first necked area and a second necked area spaced rearwardly from the first necked area.

3. The male luer as claimed in claim 2, wherein the valve member has a resilient, compressible portion.

4. The male luer as claimed in claim 3, wherein the valve member is contoured at said tip to complement the first necked area of the inner tubular portion.

5. The male luer as claimed in claim 4, wherein the valve member is contoured at a location spaced rearwardly of said tip to complement the second necked area of the inner tubular portion so that the valve member is substantially flush with the forward end of the inner tubular portion in a sealed condition.

6. The male luer as claimed in clam 3, wherein the resilient member is a spring or is of elastomeric material.

7. The male luer as claimed in claim 1, further including a housing having an outer tubular portion with a rear end and a forward open end, the tubular conduit and the resilient member being disposed at least partially within the housing.

8. The male luer as claimed in claim 7, wherein the housing is generally cylindrical in shape and contains threads on an internal surface of the outer tubular portion for engaging complementary threads on the female luer connector.

9. The male luer as claimed in claim 1, wherein the resilient member and the valve member are formed integrally.

10. The male luer as claimed in claim 9, wherein the resilient member and the valve member are of elastomeric material.

11. A male luer for connection with a female luer valve having a contact surface, the male luer comprising:
    a housing having a forward end and a rearward end; and disposed within the housing: a first tubular member positioned within the housing and having a forward end and a rearward end;
    a resilient member with forward and rearward ends disposed coaxially with the first tubular member, the resilient member being movable between a compressed, retracted position and an extended position; and a valve member disposed at the forward end of the resilient member for openable closure of the male luer during such movement; wherein when the male luer is inserted into the female luer the contact surface of the female luer motivates the resilient member into the compressed position to open the forward end of the male luer and permit liquid flow through and between the luers, with the liquid transiting the male luer traveling in a generally axial path through the tubular conduit of the male luer to or from the female luer.

12. The male luer as claimed in claim 11, wherein the housing is generally cylindrical and defines an internal chamber and contains threads on its surface for engaging complementary threads on the female luer connector.

13. The male luer as claimed in claim 11 wherein the resilient member is disposed internally of the first tubular member with the rearward ends of both in contact with each other and with a portion of the housing, such that the first tubular member secures the rearward end of resilient member against movement.

14. The male luer as claimed in claim 13 wherein the first tubular member also includes means to guide movement of the resilient member during compression and decompression of the latter.

15. The male luer as claimed in claim 11, wherein the first tubular member is comprised of rigid molded material.

16. The male luer as claimed in claim 11, wherein the resilient member and the valve member are formed integrally.

17. The male luer as claimed in claim 16, wherein the resilient member and the valve member are made of elastomeric material.

18. The male luer as claimed in claim 11 wherein the first tubular member is disposed internally of the resilient member and acts to guide movement of the resilient member upon compression or decompression.

19. The male luer as claimed in claim 11 further comprising a second tubular member wherein the resilient member is disposed internally of the second tubular member with the rearward ends of both in contact with each other and with a portion of the housing, such that the second tubular member secures the rearward end of resilient member against movement.

20. The male luer as claimed in claim 11 further comprising the resilient member being responsive to its contact with the contact surface of the female luer during engagement between the luers, responsiveness comprising compression of the resilient member effecting opening of the male luer to permit fluid flow between and through the luers.

21. The male luer as claimed in claim 20 wherein the contact surface to which the resilient member is responsive comprises a post within the female luer.

22. The male luer as claimed in claim 20 wherein the contact surface to which the resilient member is responsive comprises a forward face of the female luer.

23. The male luer as claimed in claim 20 wherein the contact surface to which the resilient member is responsive comprises an internal surface of the female luer.

24. The male luer as claimed in claim 20 where the responsiveness further comprises decompression of the resilient member upon disengagement of the luers thereby effecting closing of the male luer to prevent fluid flow through the male luer.

25. The male luer as claimed in claim 11 wherein the resilient member further comprises a closeable valve at an end thereof, and upon engagement with the female luer the resilient member deforms to open the valve and upon disengagement with the female luer deformation of the resilient member is reversed effecting closure of the valve.

26. The male luer as claimed in claim 11 further comprising the resilient member having axial movement within the male luer upon compression or decompression and guide means external of the resilient member of the valve member cooperating with guided means integrated into the resilient member or valve member for guidance of the axial movement of the resilient member.

27. The male luer as claimed in claim 26 further comprising a sleeve slidably mounted over said first tubular member between the first tubular member and outer tubular wall, the sleeve trapping the guided means.

28. A male luer as claimed in claim 11 wherein the housing contains securing means adjacent the forward end for releaseable engagement with the female luer for releaseably securing the luers together.

29. A male luer as claimed in claim 11 wherein the first tubular member contains securing means adjacent the forward end for releaseable engagement with the female luer for releaseably securing the luers together.

30. A male luer as claimed in claim 11 wherein the resilient member contains securing means adjacent the forward end for releaseable engagement with the female luer for releaseably securing the luers together.

31. The male luer as claimed in claim 11 further comprising the first tubular member extending co-axially within the housing from the rear end and projecting outwardly beyond the forward end of the outer tubular wall, the first tubular member having a second diameter less than said first diameter and having at least one axially extending slot and a forward end having a valve seat.

32. A male luer comprising:

a housing;

a resilient member with first and second ends that can be elastically displaced that is contained within the housing;

a tubular member with a forward end and a rearward end contained between the housing at a position located coaxially between the housing and the resilient member wherein the forward end of the tubular member contains a recess that creates a necked area;

a valve member abutting the resilient member and sealing the forward end of the tubular member, the resilient member being movable between an extended position in which the valve member is in sealing engagement with the forward end of the tubular member, and a retracted position in which the valve member is refracted rearwardly form the forward end;

such that when the male luer is inserted into a female luer the female luer drives the resilient member into a compressed position to open the forward end of the male luer and permit flow from one luer to another whereby liquid exiting the male luer travels in a generally linear path through the tubular member of the male luer and enters the female luer.

33. The male luer as claimed in claim 32, wherein the housing is generally cylindrical in shape and contains threads on its surface for engaging complimentary threads on the female luer.

34. The male luer as claimed in claim 32, wherein the valve member is a plug that seals the tubular member at the forward end.

35. The male luer as claimed in claim 34, wherein the plug is made of elastomeric material.

36. The male luer as claimed in claim 32, wherein the tubular member and sliding sleeve are of rigid molded plastic.

37. The male luer as claimed in claim 32, wherein the resilient member and valve are of elastomeric material.

38. The male luer as claimed in claim 32, wherein the resilient member is a spring.

39. The male luer as claimed in claim 32, wherein the resilient member is integrally connected to the housing.

* * * * *

UNITED STATES PATENT AND TRADEMARK OFFICE
CERTIFICATE OF CORRECTION

PATENT NO. : 6,964,406 B2 Page 1 of 1
DATED : November 15, 2005
INVENTOR(S) : Mark C. Doyle It is certified that error appears in the above-identified patent and that said Letters Patent is hereby corrected as shown below:

Column 2,
Line 19, delete "a inner" and insert -- an inner --.

Column 3,
Line 63, delete "contract" and insert -- contact --.

Column 4,
Line 1, delete "contract" and insert -- contact --.

Column 6,
Line 45, delete "of smaller" and insert -- of a smaller --.

Column 7,
Line 18, delete "can any" and insert -- can be any --.

Column 9,
Line 15, delete "shown" and insert -- show --.
Line 62, delete "clam" and insert -- claim --.

Column 12,
Line 23, delete "form" and insert -- from --.

Signed and Sealed this

Ninth Day of May, 2006

JON W. DUDAS
*Director of the United States Patent and Trademark Office*